US011123232B2

(12) United States Patent
Haire et al.

(10) Patent No.: US 11,123,232 B2
(45) Date of Patent: *Sep. 21, 2021

(54) INCONTINENCE SYSTEM

(71) Applicants: Glen Haire, Owensboro, KY (US);
Doug Jackson, New Albany, IN (US);
John Naber, Goshen, KY (US)

(72) Inventors: Glen Haire, Owensboro, KY (US);
Doug Jackson, New Albany, IN (US);
John Naber, Goshen, KY (US)

( * ) Notice: Subject to any disclaimer, the term of this patent is extended or adjusted under 35 U.S.C. 154(b) by 171 days.

This patent is subject to a terminal disclaimer.

(21) Appl. No.: 16/404,136

(22) Filed: May 6, 2019

(65) Prior Publication Data
US 2019/0262192 A1    Aug. 29, 2019

Related U.S. Application Data

(63) Continuation of application No. 14/872,186, filed on Oct. 1, 2015, now Pat. No. 10,322,036.

(60) Provisional application No. 62/059,464, filed on Oct. 3, 2014.

(51) Int. Cl.
| | |
|---|---|
| *A61F 13/42* | (2006.01) |
| *A61B 5/00* | (2006.01) |
| *A61F 13/15* | (2006.01) |
| *A61B 5/20* | (2006.01) |
| *A61B 5/01* | (2006.01) |
| *A61B 5/145* | (2006.01) |
| *A61B 5/1455* | (2006.01) |
| *A61B 5/11* | (2006.01) |

(52) U.S. Cl.
CPC .............. *A61F 13/42* (2013.01); *A61B 5/002* (2013.01); *A61B 5/207* (2013.01); *A61B 5/6808* (2013.01); *A61F 13/15577* (2013.01); *A61B 5/01* (2013.01); *A61B 5/112* (2013.01); *A61B 5/1117* (2013.01); *A61B 5/14532* (2013.01); *A61B 5/14539* (2013.01); *A61B 5/14542* (2013.01); *A61B 5/14552* (2013.01); *A61B 5/6823* (2013.01); *A61B 2503/08* (2013.01); *A61B 2560/0252* (2013.01); *A61B 2562/029* (2013.01); *A61F 2013/424* (2013.01)

(58) Field of Classification Search
CPC ........ A61B 5/207; A61B 5/6808; A61F 13/42
See application file for complete search history.

(56) References Cited

U.S. PATENT DOCUMENTS

| | | | |
|---|---|---|---|
| 7,053,781 B1 | 5/2006 | Haire et al. | |
| 7,250,547 B1 * | 7/2007 | Hofmeister | ............. A61F 13/42 340/573.5 |
| 7,977,529 B2 | 7/2011 | Bergman et al. | |
| 7,996,148 B2 | 8/2011 | Bergman et al. | |
| 8,145,422 B2 | 3/2012 | Bergman et al. | |
| 8,788,195 B2 | 7/2014 | Bergman et al. | |
| 9,107,776 B2 | 8/2015 | Bergman et al. | |
| 9,224,102 B2 | 12/2015 | Bergman et al. | |
| 9,283,123 B2 | 3/2016 | Bergman et al. | |
| 9,314,381 B2 | 4/2016 | Bergman et al. | |
| 9,646,073 B2 | 5/2017 | Bergman et al. | |
| 9,665,639 B2 | 5/2017 | Bergman et al. | |
| 9,713,554 B2 | 7/2017 | Bergman et al. | |

(Continued)

*Primary Examiner* — Gary Jackson
*Assistant Examiner* — Zahed Kabir
(74) *Attorney, Agent, or Firm* — Chris Tanner; FYPA PLLC

(57) ABSTRACT

An incontinence detection device and system is disclosed.

18 Claims, 18 Drawing Sheets

(56) References Cited

U.S. PATENT DOCUMENTS

| | | | |
|---|---|---|---|
| 9,913,608 B2 | 3/2018 | Bergman et al. | |
| 2007/0100666 A1* | 5/2007 | Stivoric | A61B 10/0012 |
| | | | 705/3 |
| 2008/0058740 A1* | 3/2008 | Sullivan | A61F 13/42 |
| | | | 604/361 |
| 2012/0268278 A1* | 10/2012 | Lewis | A61B 5/208 |
| | | | 340/573.5 |
| 2014/0200538 A1* | 7/2014 | Euliano | G01N 27/121 |
| | | | 604/361 |
| 2014/0276504 A1* | 9/2014 | Heil | G06K 7/10366 |
| | | | 604/361 |
| 2016/0095758 A1 | 4/2016 | Haire et al. | |

* cited by examiner

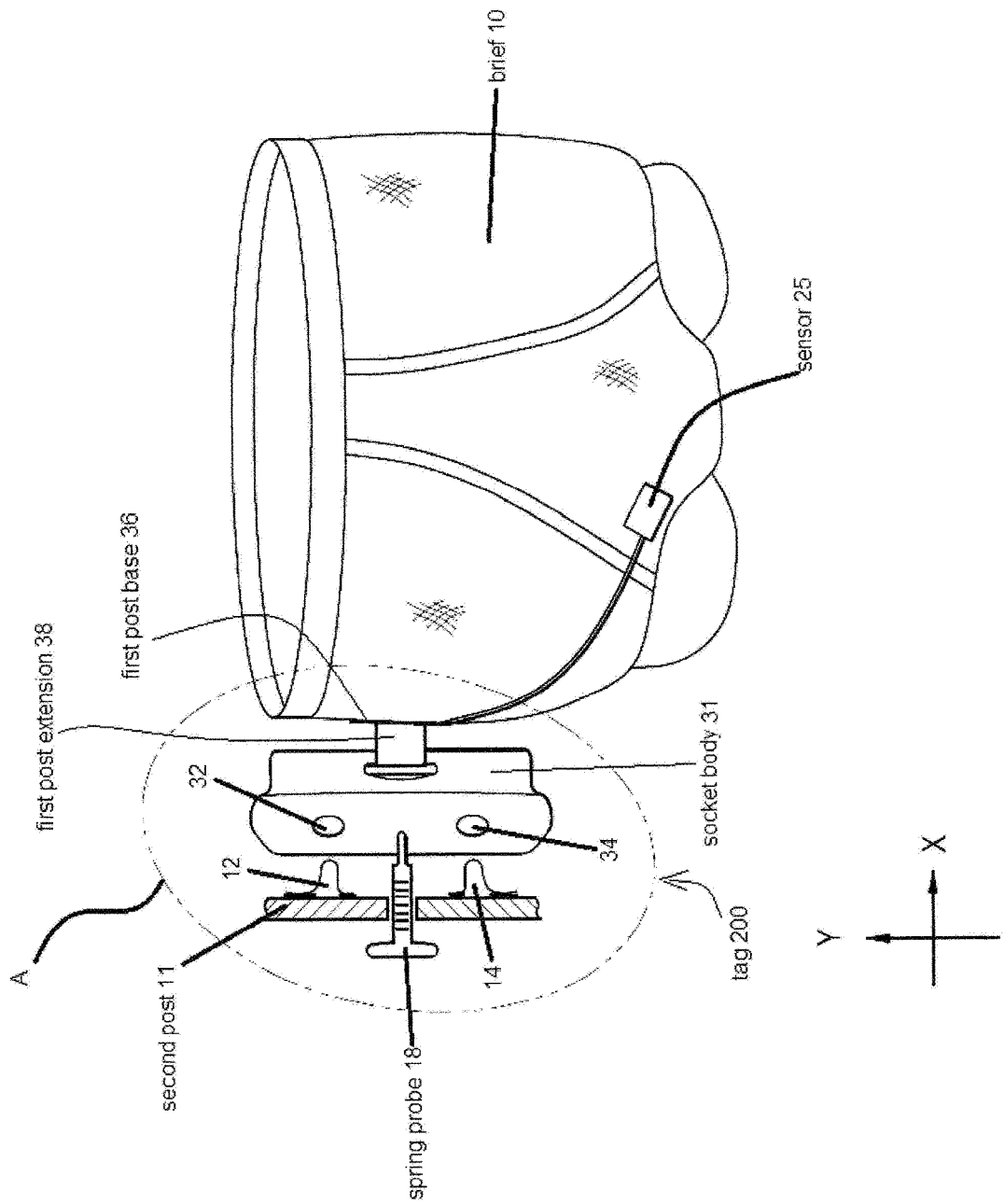

FIG. 5

Patient / Resident Data:

Current Status: _____
(Dry/Moisture Detected/Needs Changing)

Date of Most Recent Void: _____

Time of Most Recent Void: _____ AM/PM

Time Brief Changed: _____ AM/PM

Assistant who changed: _____

Avg: interval between voids: _____ (hrs) _____ (min.)
(last 10)

Tag Data: _____

Date Implemented: _____

Days until Replacement _____ locating a wetness sensor with a conductor within a underwear brief to be worn by a person suffering from incontinence configuring an electronic tag having a microcontroller and transmitter to be in mechanical connection with the brief and in electrical connection with the wetness sensor constructing the mechanical connection of a spring probe and an extension configuring the extension to protrude through the brief positioning the post inside the brief joining the extension to a post such that the tag is releaseably attached to the brief

FIG. 8

```
tcp...tion_25f60d2bc609d436_2b5d88babd117764        _ ☐ ×

Name: thundarr IP Address: fe80::d9cc:b214:c5bb:34c8%19
Name: thundarr IP Address: fe80::20ab:3285:f537:34f3%11
Name: thundarr IP Address: 10.200.203.12
Name: thundarr IP Address: 2001:0:9d38:90d7:20ab:3284:f537:34f3
 >> Enter Port Number (Default is 8888):
 _
```

FIG. 11A

REPLACEMENT DRAWING    16404136

```
tcp...tion_25f60d2bc609d436_2b5d88babd117764        _ ☐ ×

Name: thundarr IP Address: fe80::d9cc:b214:c5bb:34c8%19
Name: thundarr IP Address: fe80::20ab:3285:f537:34f3%11
Name: thundarr IP Address: 10.200.203.12
Name: thundarr IP Address: 2001:0:9d38:90d7:20ab:3284:f537:34f3
 >> Enter Port Number (Default is 8888):
 >> Server is ready for next TCP connection:
```

FIG. 11B

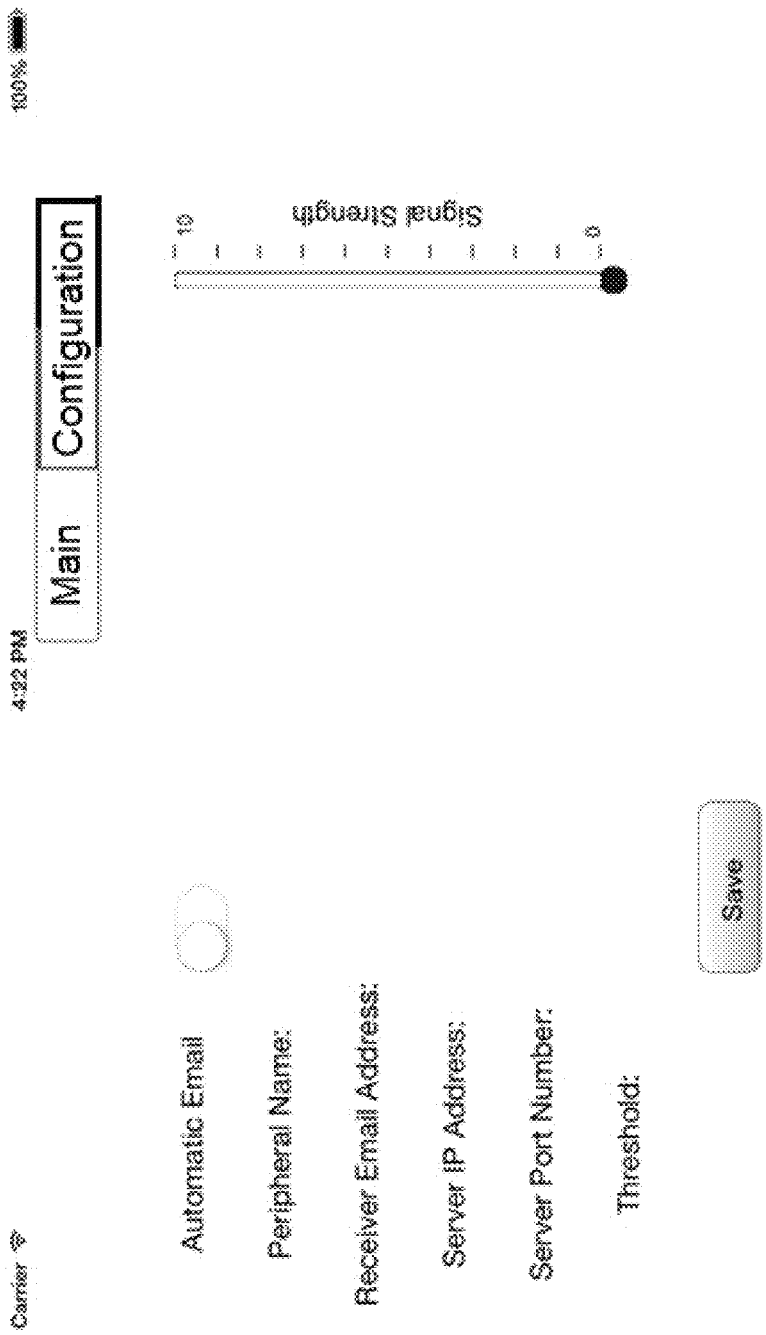
FIG. 12 (iPad configuration)

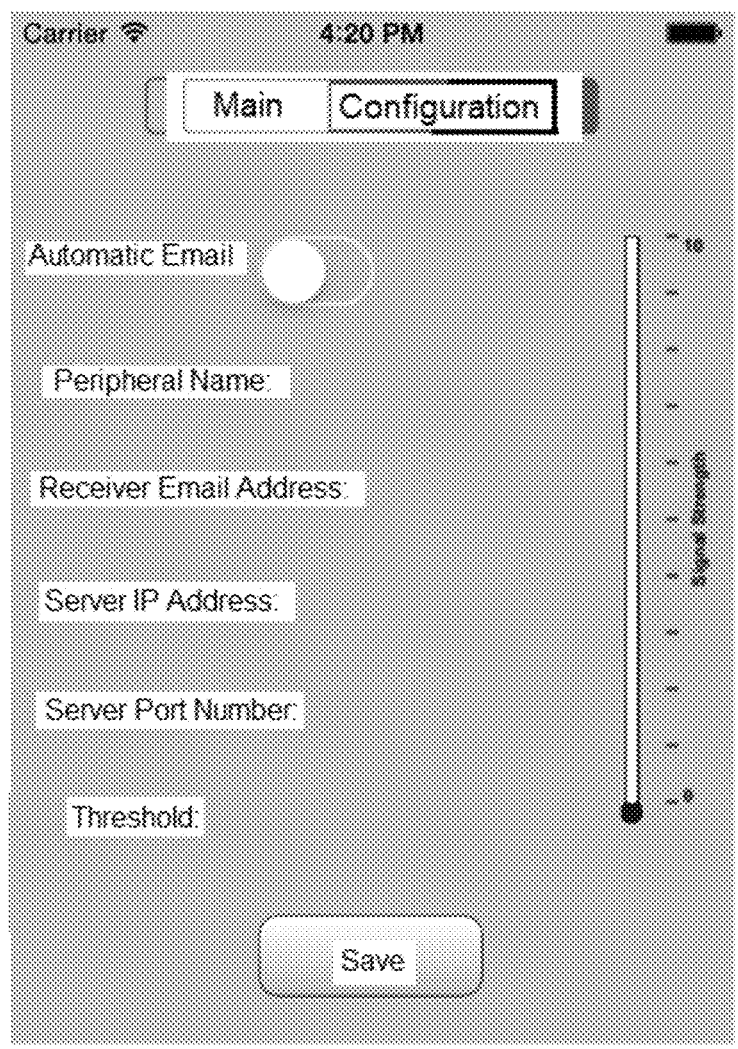
FIG. 13 (iPhone configuration)

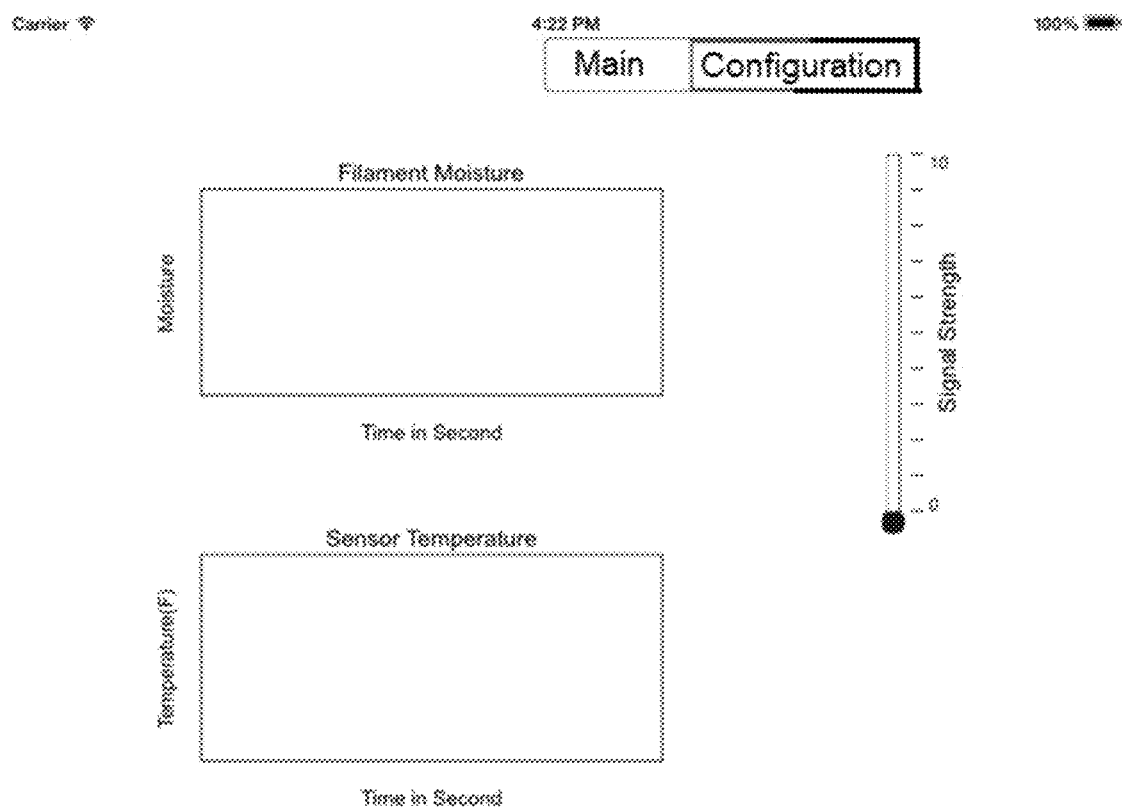
FIG. 14 (iPad)

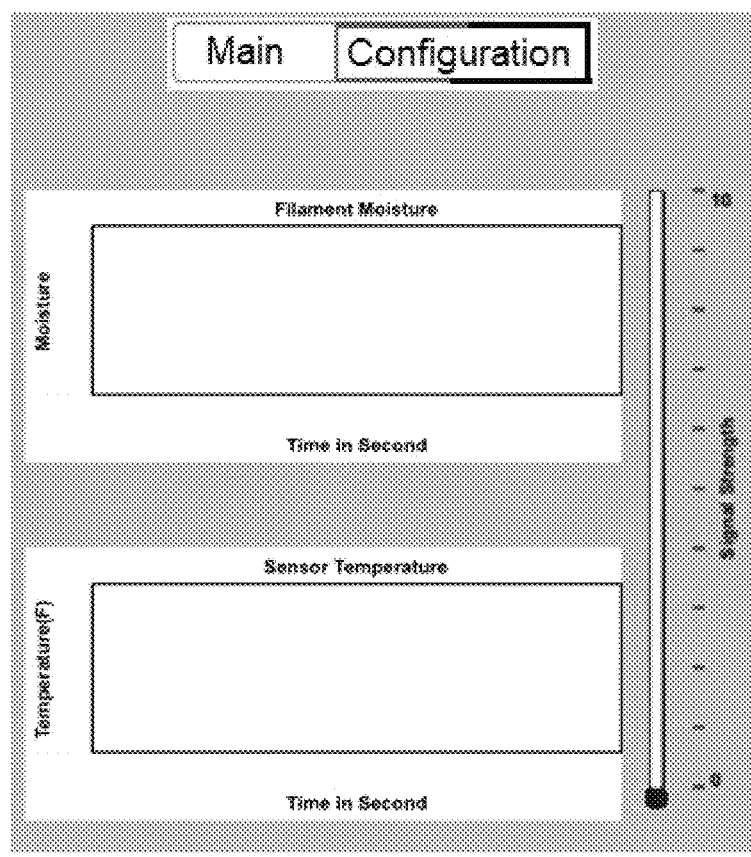
FIG. 15 (iPhone)

INCONTINENCE SYSTEM

CROSS REFERENCE TO RELATED APPLICATIONS

This application claims priority to Provisional Application No. 62\059,464 filed on Oct. 3, 2014, the entire contents of which are hereby incorporated by reference.

INVENTION

Embodiments described herein relate to the field of patient care, long term care, and care for patients who are either non-ambulatory or compromised functionally, and specifically the embodiments relate to reducing or alleviating the problem of urinary incontinence. In some embodiments, a system is provided for detecting when a patient has a wet or soiled brief that needs to be changed, and utilizes a wetness sensor embedded within the brief in electrical coma unification with a tag for transmitting signals indicative of a status of the patient's brief. Optional features of the system include additional forms of monitoring and tracking patient—or tag-related data and function.

BACKGROUND

Urinary incontinence is the loss of bladder control. While for some individuals, it is possible to reduce or stop urinary incontinence, for others it is a problem that cannot be prevented, particularly for the aged, infirm, and others who live in a long-term care setting. For patients or residents (hereafter, "patients") who are incontinent, one of the ways to provide comfort is to ensure that their briefs or diapers (hereafter, "briefs") are regularly changed following a void event. In this sense, a void event is one marked by wetness of the brief, which can be either due to urine, diarrhea, or loose stool.

A degree of urinary incontinence affects a high percentage of nursing home residents in the United States, which some have estimated at about 60%. Risk factors include impaired ambulation and immobility, physiological changes of the genitourinary system associated with aging, decreased capacity to hold urine due to reduced bladder size, reduced effectiveness of the kidneys, atrophy of pelvic and sphincter muscles resulting in an increased urgency to empty the bladder, and functional impairments suet as dementia or Alzheimer's disease. Moreover, patients are at greater risk to develop incontinence by having to wear a wet or a soiled brief for an extended period of time, without timely changing of the brief after a void event.

The effects of urinary incontinence are often significant. Besides issues of discomfort and dignity, the condition is causally related to urinary tract infections, which are the most common infection found in the nursing homes. A soiled or wet brief for a prolonged period of time increases the chances of developing a urinary tract infection. The longer a wet or soiled brief is worn, the longer bacteria will multiply and increase the severity of a urinary tract infection. On the other hand, it is possible to restore some degree of continent e to a any patients by consistently changing his or her brief within a short time of a void event, and having the knowledge of when such are event is likely to occur will facilitate that effort. Success in this area will result in tremendous savings by reducing the number of incontinent patients, reducing the severity of incontinence in certain individuals, and reducing the incidence of urinary tract infections.

Accordingly, a change in practice that results in more timely changes would reduce the extent of incontinence-related problems in long term care. Current practice in the industry is to change the briefs of incontinent patients based on a time schedule. However, this practice has substantial limitations, mainly in the sense of a lack of information about the specific-patient and his or her void status at any particular time. The management of brief changes based on a time schedule is largely guesswork, while basing it on patient notification or caregiver inspection is not consistently timely or reliable. Thus there is a need for providing real-time information to caregivers regarding when a void occurs, so they can respond quickly to change the person's brief and reduce the amount, of time that one spends wearing a wet or soiled brief. Further, realizing that an incontinent person has his or her brief changed numerous times during the day, it is important that the source of the real-time information should be either inexpensive (if it is discarded with the wet or soiled brief) and/or e sable so that it can interface with the clean brief the person wears after changing. As seen in the further teachings below, present embodiments contain elements of both reusable components as well as inexpensive sensors that can be discarded with a soiled brief upon changing.

SUMMARY OF EMBODIMENTS

An incontinence monitoring and management system according to multiple embodiments and alternatives herein is event based. Such embodiments provide timely notification regarding when a patient has experienced a void event based upon the status of wetness of his or her brief. In some embodiments, a low-cost wetness sensor s embedded within the brief, and both the brief and the sensor are disposed of at the time of changing. The practice of these embodiments will improve patient comfort, reduce the incidence of urinary tract infections, provide developing information regarding changes to the patient's medical condition (for example by tracking changes in the patter of voiding), and can also be used to document care for billing aid quality purposes.

In some embodiments an embedded wetness sensor adds only minimally to the overall cost of disposable briefs, and is easily incorporated into the manufacturing process. Further, while the electronics—referred to herein as "tag"—containing the sensor interface, signal processing, transmitter (preferably wireless antenna, and battery costs more, these components are not part of the disposable brief and can e reused. This is accomplished by connecting the tag externally to the brief and making physical and electrical connections through a releasable snap fit.

BRIEF DESCRIPTION OF THE FIGURES

The drawings, schematics, figures, and descriptions herein are to be understood as illustrative of structures, features and aspects of the present embodiments and do not limit the scope of the embodiments. The scope of the application is not limited to the precise arrangements or scales as shown in the drawings.

FIG. 1A is a perspective view of a brief or a diaper (hereafter collectively referred to as "a brief") which can be worn by a person, and upon which certain components of an incontinence monitoring and management system are located according to multiple embodiments and alternatives described herein. Hereafter, for brevity "incontinence monitoring and management system" is referred to as "incontinence monitoring system," or, simply, "System."

FIG. 5 is an example of a printout containing information that has been transmitted, recorded, processed, and/or tracked according to multiple embodiments and alternatives described herein.

FIG. 8 is a flowchart depicting a method of manufacturing the system.

FIGS. 11A and 11B show example console windows related to a server module.

FIG. 12 shows an example Configuration tab of iPad app.

FIG. 13 shows an example Configuration tab of an iPhone app.

FIG. 14 sows an example Main tab of an iPad app.

FIG. 15 shows an example Main tab of an iPhone app.

DETAILED DESCRIPTION OF PREFERRED EMBODIMENTS

Figure 1B:
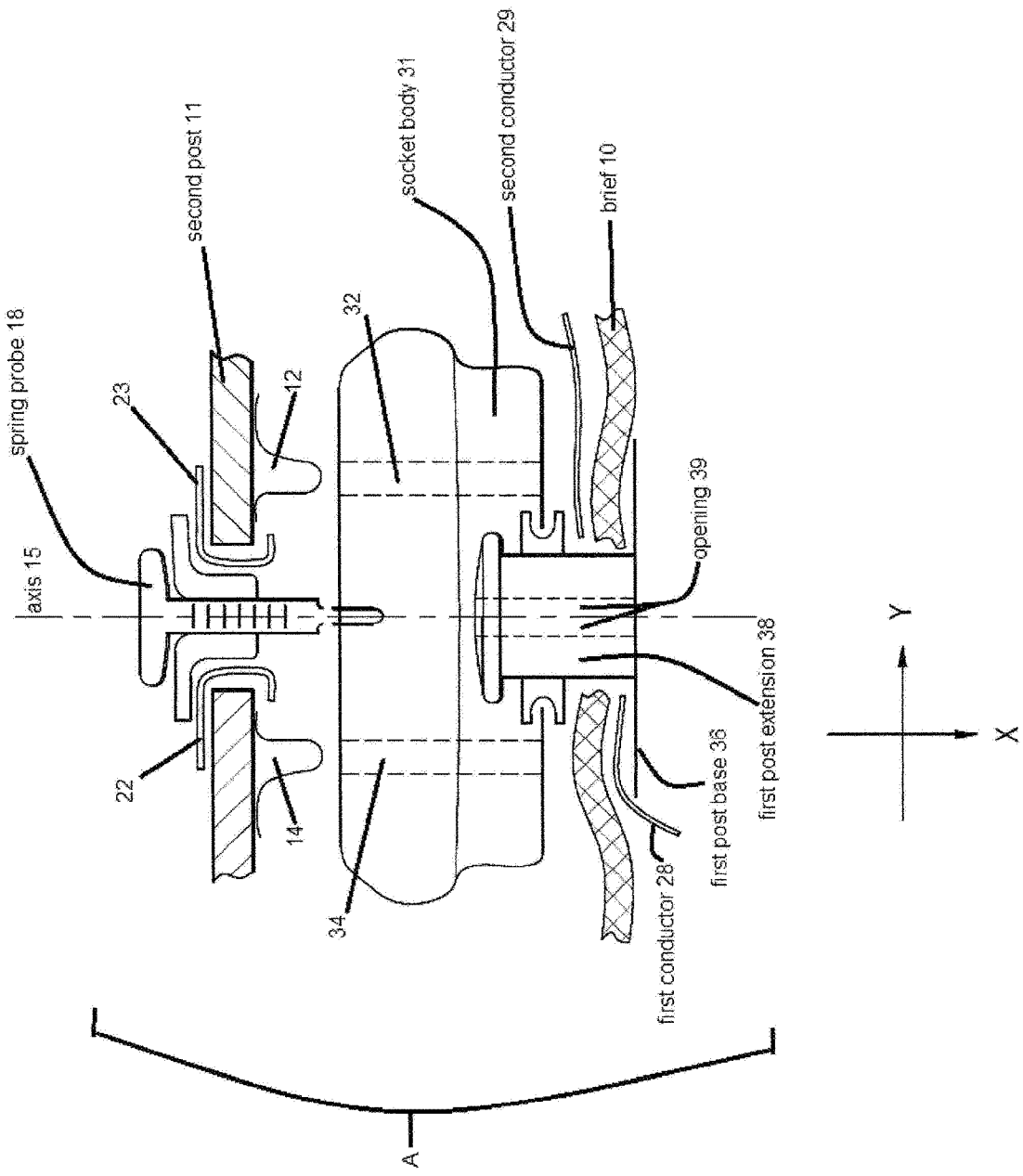
FIG. 1B is a cross section taken from region "A" of FIG. 1A, and show in components of an incontinence monitoring system, according to multiple embodiments and alternatives described herein.

In some embodiments, a tag with electronics as described herein releasably mates to a post secured to the brief using a snap fit joinder. The joining structures provide mechanical and electrical connection with the brief and sensor, wherein a mechanical snap with at least one spring loaded contact permits an electrical signal to be passed. In this way, the apparatus functions both as a mechanical/electrical connection with a sensor circuit linked by a conductor wire, and it communicates with a microcontroller via a sensor interface circuit. Additional electrical paths can be made at the contact by placing one or more additional contacts in the center of the structures that are snap fit together. Further, the apparatus allows for a thermal path to be established between the tag and the patient for temperature sensing.

FIG. 1A offers a perspective view of brief 10 with an embedded sensor. Primarily, this figure shows the main mechanical structures for accommodating connection of a tag 200 which allows the sensed information to be transmitted. Similar to a conventional brief, brief 10 contains a waistband 5, and first and second openings 6, 7 for a patient's legs. For orientation, a vertical direction marker (Y axis) and a horizontal direction marker (X axis) are provided with this figure. For example, a patient wearing brief 10, while standing, would be oriented in the upright, vertical direction denoted by Y axis.

In some embodiments, sensor 25 detects wetness conditions in the fabric of brief 10, and additional structures shown in FIG. 1A enable the transmission of signals indicative of such findings. Wetness sensor 25 (or, simply, "sensor" 25) can be positioned within brief 10 in any position suitable for detecting wetness. In some embodiments, conductor 28 is an insulated wire providing electrical connection between the sensor and the tag 200.

Brief 10 is manufactured from a fabric selected by a user. Such fabric can be selected from any of multiple options as are known in the art, and the embodiments described herein are not limited by choice of fabric. Although the fabric is conventional, certain modifications are suitable to be made in order to practice the embodiments contained herein. In some embodiments, sensor 25 is embedded within the fibers of the fabric of brief 10. In such embodiment, the sensor 25 is composed of fibers having conductive, antibacterial, and/or deodorizing properties. These fibers however do not chafe or irritate skin, and are basically undetectable by a wearer. Alternatively, sensor 25 is secured to the fabric of brief 10 by any of a number of mechanical securing options, including adhesive, hook and loop, magnetic attachment, stitching to the fabric, or other mechanical attachment means.

Figure 1C:
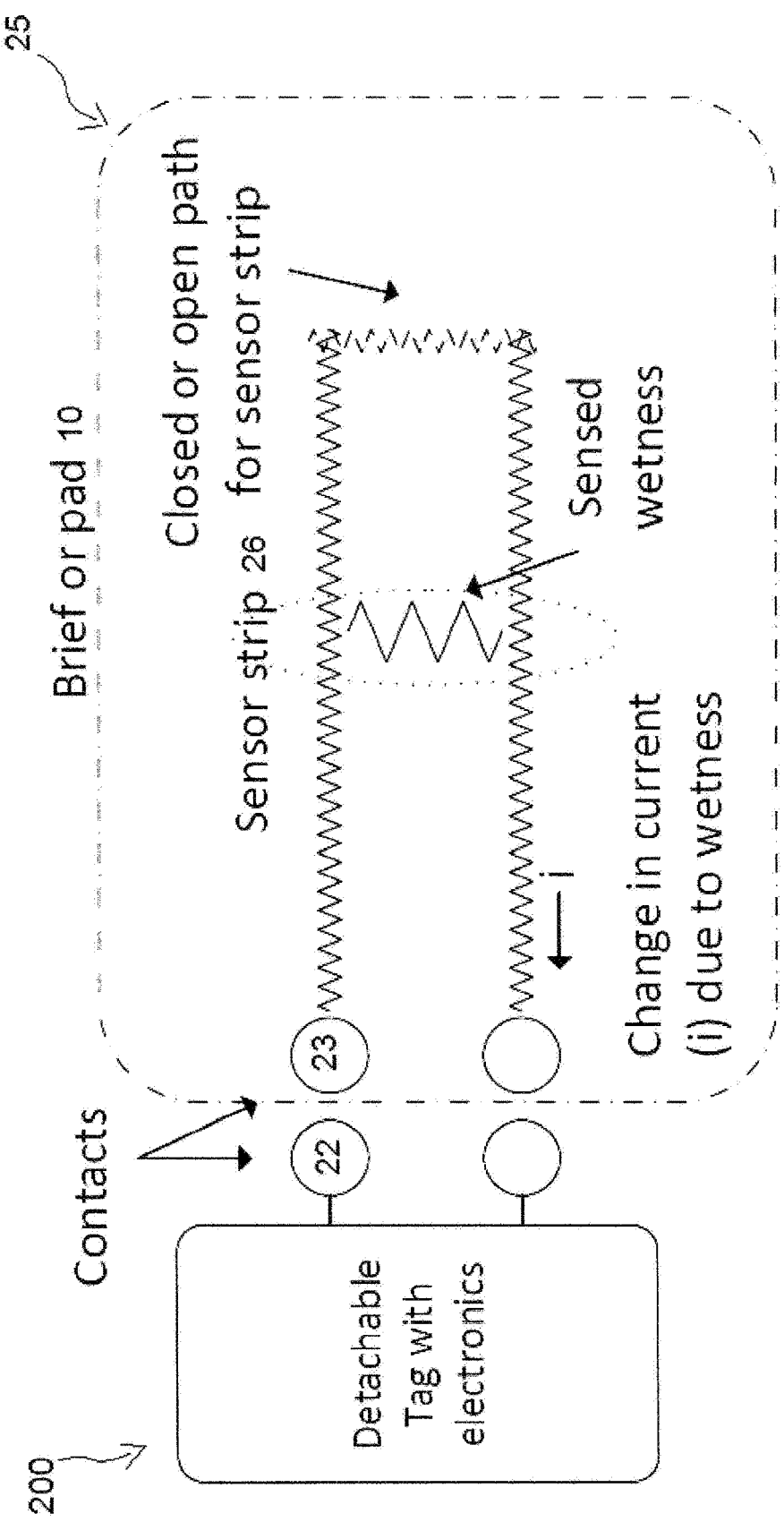
FIG. 1C shows a circuit diagram for use with the tag.

FIG. 1A further shows several other physical structures which can be employed to secure the tag to brief 10 and establish contact between conductor 28 and one or more contacts that complete a circuit. For clarity, the elements in FIGS. 1A-1C are not necessarily the exact sizes and proportions shown. Accordingly, in some embodiments a first post 36 is formed with a post extension 38. As seen in FIG. 1B, post extension 38 may include an extension opening 39 for receiving a spring probe 18 (shown in both FIG. 1A and FIG. 1B).

With reference still to FIG. 1A, the first post base 36 is positioned on the inside of brief 10, and post extension 38 protrudes through brief 10. This could be accomplished by forming an opening (not shown) in the fabric of brief 10. In some embodiments, such an opening also accommodates conductor 28 in passing from the interior of the brief 10, where it receives inputs from sensor 25, to the exterior for electrical connection with the tag via ogre or more contacts.

Although FIGS. 1A and 1B show a single post base 36 and post extension 38, this depiction is mainly for clarity, simplicity, and ease of understanding. In some embodiments, multiples posts and multiple post extensions are used. Further, in some embodiments, the tag itself which is involved in the transmission of sensed information is snap fit with first post base 36 and post extension 38, as is discussed in connection with both FIG. 1A and FIG. 1B. For example, both figures show a socket body 31, in which at least a first socket 32 is formed, and which optionally includes (as shown in the figures) a second socket 34. In the figures, sockets 32, 34 are configured and positioned so that first stud and second stud 12, 14 can be matably and removably inserted into them. FIG. 1A and FIG. 1B show the studs 12, 14 as being formed integrally with a second post 11, having an opening, for accommodating the spring probe 18.

The physical and structural components for the tag are further illustrated in FIG. 1B, which is a cross-section of region "A" shown in FIG. 1A, and in which longitudinal axis 15 provides a reference point. For additional perspective, it will be noticed that line Y of FIG. 1A is rotated 90° to horizontal in FIG. 1B, and likewise line X is rotated 90° to vertical. Starting at the fabric end, i.e., brief 10, in some embodiments first post base 36 is positioned internal of brief 10, as shown, with post extension 38 protruding through an opening (not shown) in the fabric. FIG. 1B further shows post extension 38 having an opening 39 for receiving the spring probe 18, which is capable of bidirectional movement along axis 15 suitable for both engagement with the opening 39 within the post extension 38, as well as withdrawal from that opening. Various structures as are known in the art can be used to releasably secure the spring probe 18 when it enters the opening 39.

The apparatus in this way is capable of snap fitting the tag 200 together with the first post base 36 which is located within the brief 10. As with the tag itself, first post 36, post extension 38, and other structures, which are involved with achieving an electrical connection with sensor 25 via first conductor 28, can be positioned in a variety of locations in relation to brief 10, so that their positioning is not limited to the arrangements depicted in the drawings. Similarly, the tag 200 can be positioned other than what is shown in FIGS. 1A-1B, such as in the front center of the brief 10.

When the brief is dry, sensor 25 and conductor 28 for an incomplete circuit with no electrons flowing to the tag 200. When a significant void event occurs, it will result in a threshold amount of wetness causing the circuit to be completed acting as a switch to produce a flow of electrons to the tag 200. Thus, the output of the sensor in this fashion produces a signal that can be transmitted by the tag 200. Conversely, while the brief is relatively dry, i.e., no void since last changing, electron flow is not activated and no signal indicative of wetness is transmitted.

FIG. 1C provides an example of a circuit diagram for use with the tag 200 according to multiple embodiments and alternatives. Sensor 25 includes a microcontroller (not shown) which applies a voltage at selected intervals through a resistor to a conductive strip 26, providing an open or closed path. In some embodiments, a circuit 24 includes first and second contacts 22, 23, respectively. The resistor connection to strip 26 represents a node. Preferably, a second conductive strip (not shown) is also arranged parallel to the first strip and connected to circuit ground. In this configuration, wetness associated with a void event causes an increased voltage drop across the resistor which decreases the voltage at the node. In some embodiments, the voltage at the node is measured, and this value indicative of wetness is then transmitted (e.g. wirelessly) via a communication interface to a device. Accordingly, a change in signal produced by a change in particular measurable electrical property indicates wetness. It will be appreciated by persons of skill in the art that various properties can be measured and transmitted as an indicator of wetness, which may be proportional or inversely proportional. The scope of embodiments and alternatives herein is not limited to a particular measured property.

In certain embodiments, sensor 25 comprises an adjustable wetness sensitivity control which can also be tailored to the specific individual. Certain embodiments provide a self-adjusting algorithm responsive to a person's wetness threshold, below which no signal is sent, to help reduce the incidence of false reports of wetness as might be associated with perspiration.

In certain embodiments, though not required, additional fixtures are utilized to further secure the fit between these members, namely the joinder of first and second studs 12, 14, respectively, with first and second sockets 32, 34, respectively within the socket body 31. Again, various structures as are known in the art can be used to releasably studs 12, 14 within sockets 32. As previously stated, studs 12, 14, can be formed integrally with the second post 11. According to FIGS. 1A and 1B, second post 11 contains an orifice 19 through which spring probe 18 is configured to fit. This allows the spring probe 18 to have a track along which it can move bidirectionally as it mates with the post extension 38 and is released from that extension. The mechanical and physical structures needed for joining the tag 200 to the first post 36 enable the pieces to be snap fated together when the brief 10 is being worn, and then released when the brief 10 is changed.

The remaining structures depicted in FIG. 1B are primarily electrical in nature. With reference to as area of the drawing proximal to the fabric, first conductor 28 is shown, which is also in direct electrical communication with sensor 25 which provides the input to be transmitted. When spring probe 18 mates with post extension 38, along with studs 12, 14 and their offsetting sockets, 32, 34, it brings the first conductor 28 into electrical communication with second conductor 29.

Figure 2A:
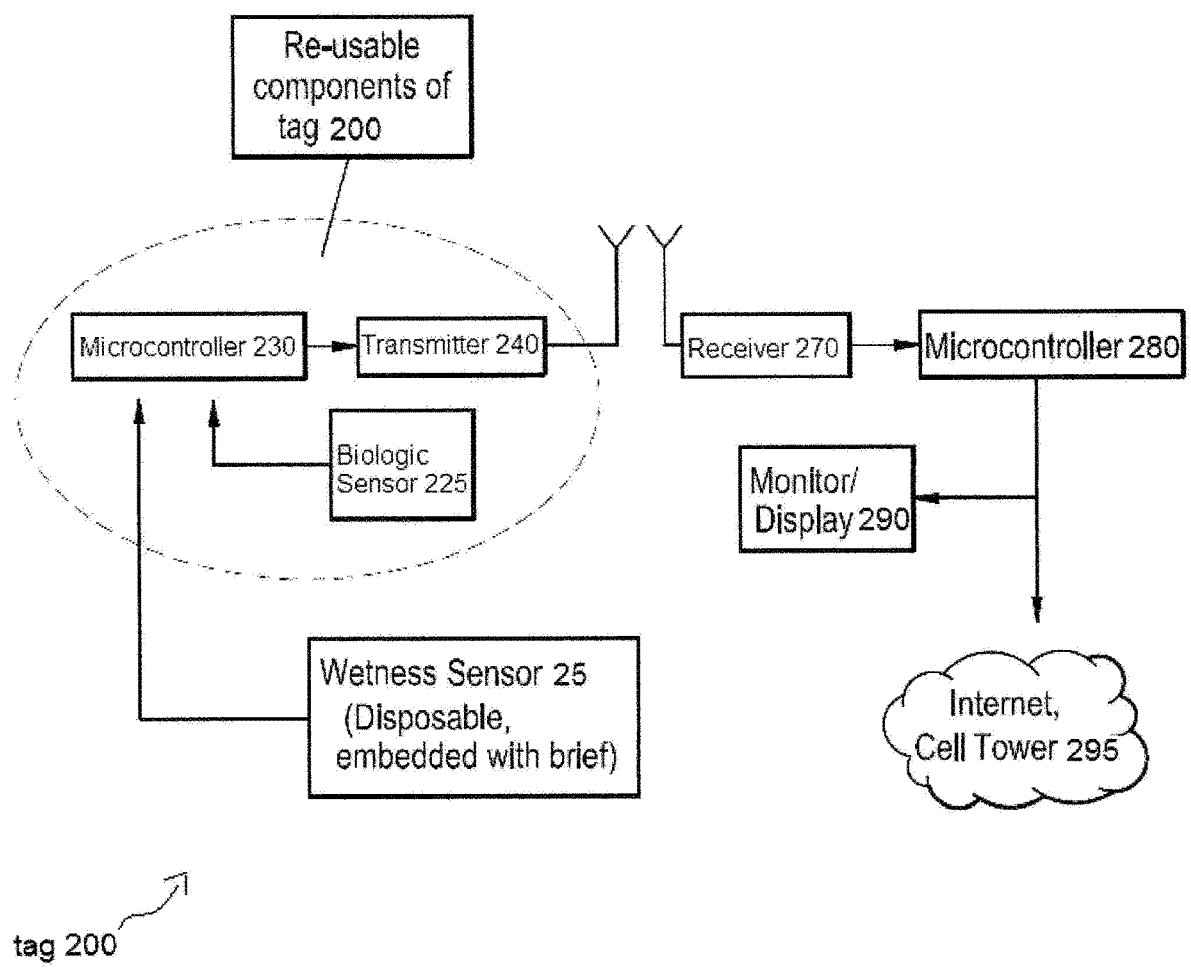
FIG. 2A is a block diagram showing the relationship of certain components of an incontinence monitoring system, according to multiple embodiments and alternatives described herein.

FIG. 2A is a block diagram that includes tag 200, which is responsible for receiving inputs from sensor 25 and transmitting signals which are received by other devices downstream. In some embodiments, tag 200 is reusable, such that the electronics contained there are easily fitted with and otherwise connected to the inexpensive wetness sensor embedded within a new brief upon changing. Accordingly, tag 200 acts as a communication interface to enable data transmission received as inputs from sensor 25, and it includes microcontroller 230, transmitter 240, and antenna 250.

The communication interface can use any of a number of various communications protocols, and transmission is accomplished either through a wired connection or wirelessly, but preferably wirelessly. Examples of such protocols are known in the art, and include but are not limited to radio frequency, infrared or microwave connection; near-field electromagnetic connection; cellular telephone network; phone line; power line; Ethernet; and universal serial bus (USB) interface.

On the receiving end, receiver 270 can optionally be a base station or router configured to receive Bluetooth wireless transmissions from tag 200. At this end, the transmission and receipt of the transmitted signal can be facilitated by antenna 260. In some embodiments, receiver 270 includes a cellular radio for transmitting data inputs originating from the sensor onto a cellular network 295 as SMS notifications, or messages can also be transmitted by email or cloud upload. Alternatively, a near-field electromagnetic induction system is utilized for short range wireless corer communication by coupling a non-propagating magnetic field between respective devices having a transmitter coil (not shown) for modulating the magnetic field to influence the signal and a receiver coil (not shown) establishing an inductive coupling link.

With further reference to FIG. 2A, in certain embodiments a separate microcontroller 280 is configured to pass incoming signals from receiver 270 to other devices, which include display 290 which can be a computer monitor, a liquid-crystal display (LCD), or the like. The information on the display is provided substantially in real-time to be viewed by a caregiver at the facility, who can then respond following a void event to change the person's brief. Or, by seeing on the display that no such event has occurred since the last changing, that caregiver will know it is unnecessary to check the patient to see if there has been a void event, thus promoting efficiency and time savings. In addition to on-site display of information, the system can be configured according to known communication protocols for information to be sent over the Internet 295 or other networks to more remote receiving devices, either for storage or further processing and review.

It is to be understood that other conditions can be sensed besides wetness conditions. As FIG. 2A indicates, other biologic sensor(s) 225 can be incorporated either within brief 10, or tangent to brief 10 provided that such sensors are located in close enough proximity to the body of the patient to be able to detect conditions of interest. In some embodiments, biologic sensors are contained within tag 200 itself. Biologic sensors may include, for example, temperature sensors, pulse oximeters; pH sensors; blood glucose monitors; and urinalysis for proteins, ketone nitrites, and like indicators.

Figure 2B:
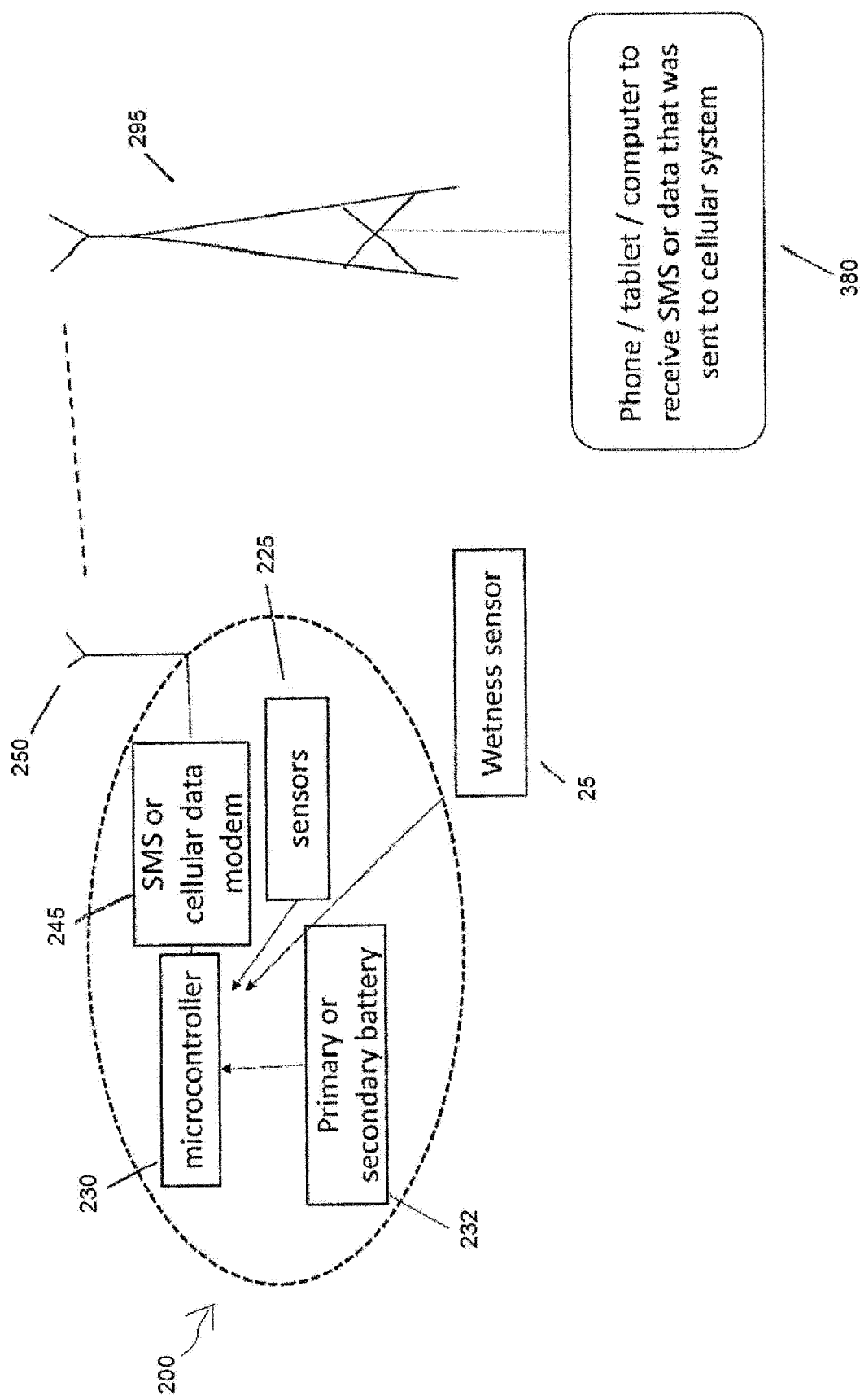
FIG. 2B is another block diagram showing additional relationships of components of an incontinence monitor system described herein.

FIG. 2B is a block diagram showing the relationship of certain components of an incontinence monitoring system which sends sensor data from the brief directly to a call tower as an SMS message. In some embodiments, where limited wireless infrastructure may be desired, the tag 200 includes a battery 232, microcontroller 230, and cellular data modem 245 for sending SMS messages coded to represent sensed data, such that the function of tag 200 is analogous to a cell phone transmitting data text messages. Thus, the data and messages are capable of being received by various devices, which may include a phone/tablet/computer, via a network either wirelessly by cellular link or through other Internet connection.

Figure 3:
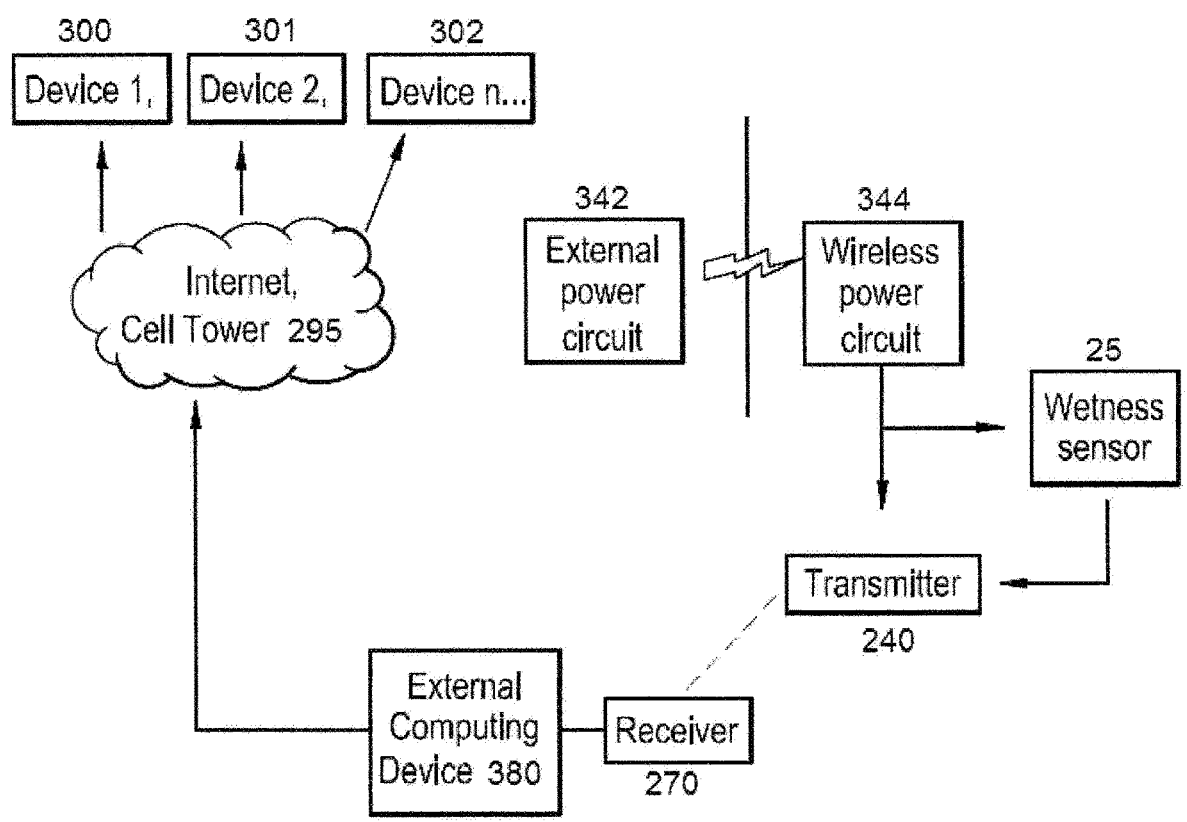
FIG. 3 is a block diagram showing the relationship of certain components of an incontinence monitoring system, according to multiple embodiments and alternatives.

FIG. 3 provides a block diagram of components which are directly or indirectly connected to sensor 25, with variations on the system configuration for transmitting data indicative of patient condition over network, such as via the Internet or cell phone tower. For the efficient review of the disclosure, like reference numerals have been used to identify like components in FIGS. 2-4. The system is configured for the transmitter 240 of tag 200 to communicate, preferably wirelessly, with an external receiver 270, as shown. Again, transmitter 240 care be equipped with any one or more of USB; serial port; Ethernet port; radio frequency, microwave, or infrared communication short range channels; or optionally near-field electromagnetic communication capability.

According to multiple embodiments and alternatives, receiver 270 is connected to an external computing device 380. Without limitation, device 380 can be either a personal computer, tablet computer, network router, web-enabled server, smart phone with computing and data storage/transfer capabilities, or the like. Device 380 can be utilized to transfer information over the Internet or via cell phone 295 as previously described, to one or more remote devices 300, 301, and 302, respectively. In some embodiments, device 380 contains a networking module to facilitate a wireless connection to the Internet 295 according to various known protocols and pathway configuration. Without limitation, methods for Internet connectivity also include standard cable connectors such as RJ-45 providing Ethernet connections. When connected in any acceptable fashion, data from transmitter 240 to receiver 270 is distributed to any or all of devices 300, 301, 302, as data packets which are sent according to one or more of several protocols as selected by a user, for example, Transmission Control Protocol/Internet protocol (TCP/IP).

Continuing with FIG. 3, one mode for providing a source of power to tag 200 includes linking an external power circuit 342 to a wireless power circuit 344 of the tag, through an inductive coupling connection as known in the art, e.g., a radio frequency charging coil (not pictured) of external circuit 342 coupled inductively to wireless power circuit 344. Alternatively, a power source for tag 200 can be a battery as shown in FIG. 4, which can be either disposable or rechargeable.

Figure 4:
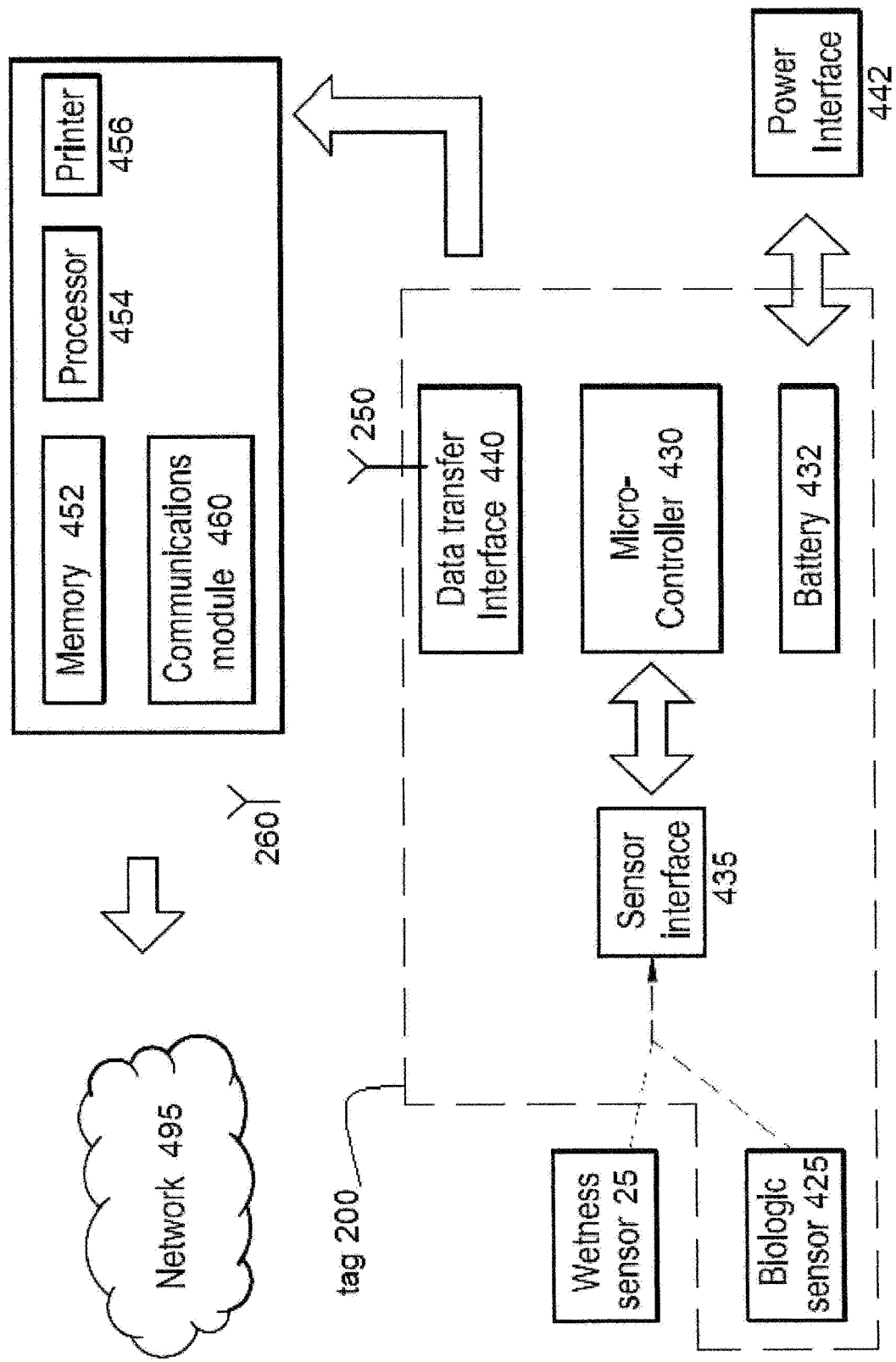
FIG. 4 is a block diagram showing the relationship of certain components of an incontinence monitoring system, according to multiple embodiments and alternatives described herein.

FIG. 4 is a block diagram that incorporates some components of FIGS. 2A-2B in relation to other optional system components. Tag 200 communicates with either or both of wetness sensor 25 and biologic sensor 425, via a sensor interface within the tag. Signal transmission is also accomplished through microcontroller 430, which accepts sensor data indicative of the condition of a patient. Microcontroller 430 then relays such data to data transfer interface 440 which can be coupled to antenna 250, for transmitting the signals to a data storage and processing sub-system 450 having an antenna 260 as well its own communications module 460 for handling incoming and outgoing signals.

Module 460 can utilize any of a number of various communications protocols that have been described herein through either a wireless connection or wired means. In some embodiments, sub-system 450 is equipped with memory 452, processor 454, and printer 456. Memory can be configured as either volatile or non-volatile memory, and includes in non-limiting fashion random-access memory (RAM), programmable read-only memory (PROM), flash memory, and other forms of database storage as well as any of a number of database management software tools for searching as would be typical for use with an electronic health record. Connection over network 495 is optionally a public network using standard broadband transmission connected to various devices in multiple facilities and locations. Alternatively, network 495 is a private network of devices and clients linked over a local area network over a dedicated network connection.

Processor 454 is used for interpreting, sorting, and aggregating the received data. For example, machine-readable program instructions stored on processor 454 may be configured to interpret a "1" value to represent a wet or soiled brief, while a "0" value is interpreted to represent that no void event has occurred since the most recent changing. Each tag 200 has unique identifier that enables the system to associate the information to the particular patient with that tag.

In some embodiments, sub-system 450 includes printer 456 for providing a visual record of status obtained from either sensors 25, 425 or from the tag itself. For example, FIG. 5 shows a sample printout 510 containing information that has been transmitted, recorded, processed, or tracked according to multiple embodiments and alternatives which are within the scope of the teachings herein. The printout 510 is divided into two different informational regions: one being patient-oriented 512 and the other being tag-oriented 514. To facilitate the time- and event-based nature of the system, sub-system 450 is further provided with a real-time clock to provide a time stamp to show when the most recent void occurred, and when the most recent changing occurred. For the latter data entry point, the time of change can be inferred based upon when the spring probe 18 of FIG. 1A and FIG. 1B is disconnected from the post extension 38.

Optionally, tracked information is aggregated and further processed to provide patient-specific information on average interval between voids, for example based upon the last ten (10) such events, or any suitable sample size as desired. This can prove helpful in predicting future events or establishing a pattern of knowing when to look for the next such event. Though not shown FIG. 4, other information tracked and listed may include the current status of the patient: whether "dry" (no voids since most recent changing), or "wetness detected," including an indication of the duration since this finding occurred. There are various ways to depict the status as can be chosen by the user, for example as visual piece of information or an icon with a bubble darkened next to one of several optional levels to indicate the status.

Although they are preferably reusable, it is anticipated that tags will need to be replaced eventually. Also, it is possible for tags to become lost or misplaced. Thus, it will often be useful to track the status of the tag itself. In some embodiments, this is accomplished by recording the date a tag was first put into use and otherwise implemented. This is accomplished by assigning a unique identifier to a particular tag. From that point, all data associated with that identifier is linked to the particular tag. A typical tag life cycle can be determined and used for calculating and showing how many days until replacement will be needed for a particular tag. It is also possible to tack information such as the length of time since the battery was last changed or replaced. Tags can also be equipped with a function capable of responding to a query sent via Bluetooth, programmed to be directed to a specific tag based on its identifier, in which the tag associated with the identifier emits audible noise in response to the query.

Figure 6:
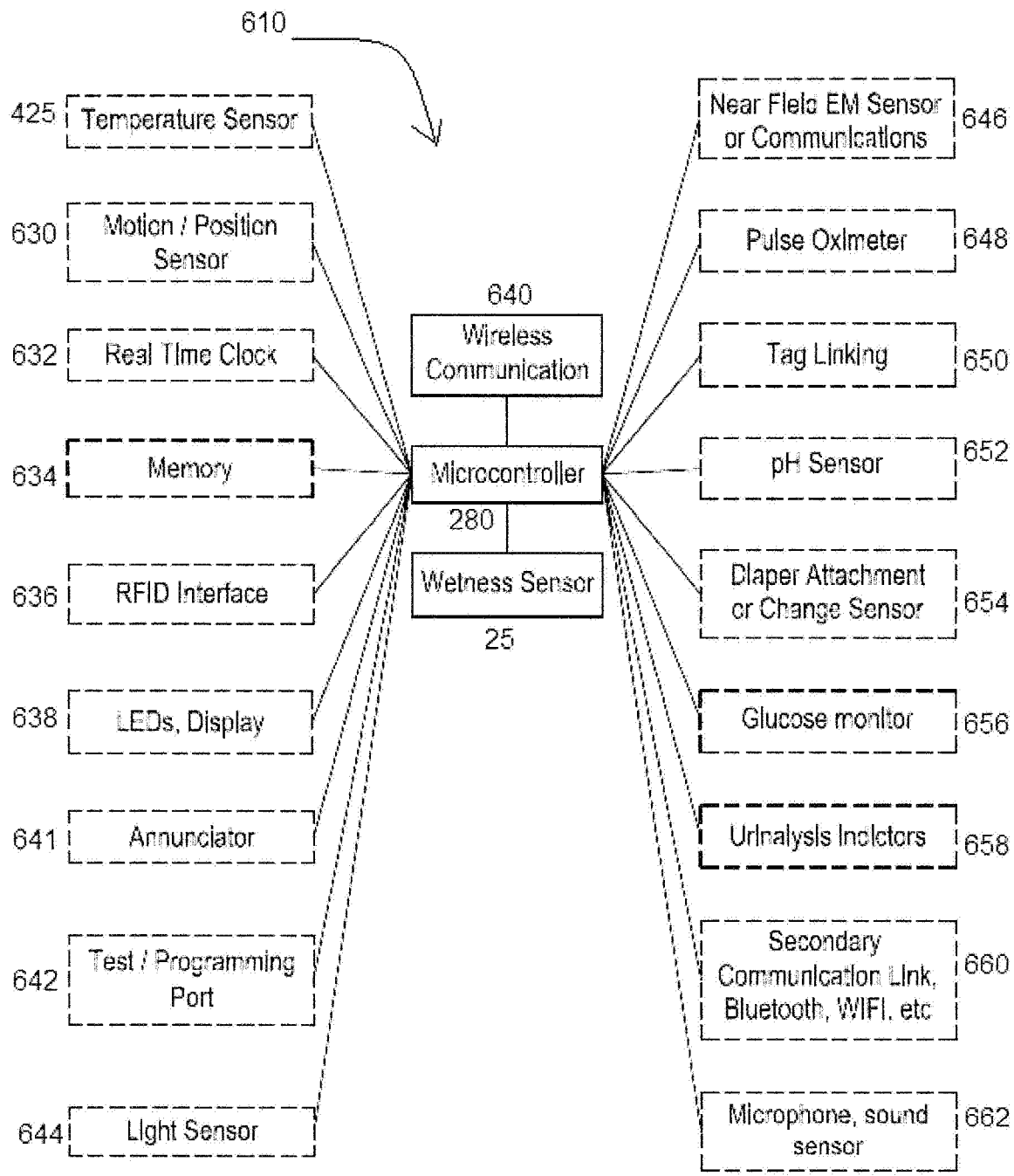
FIG. 6 is a block diagram showing the relationship of certain components of an incontinence monitoring system, according to multiple embodiments and alternatives described herein.
Figure 7:
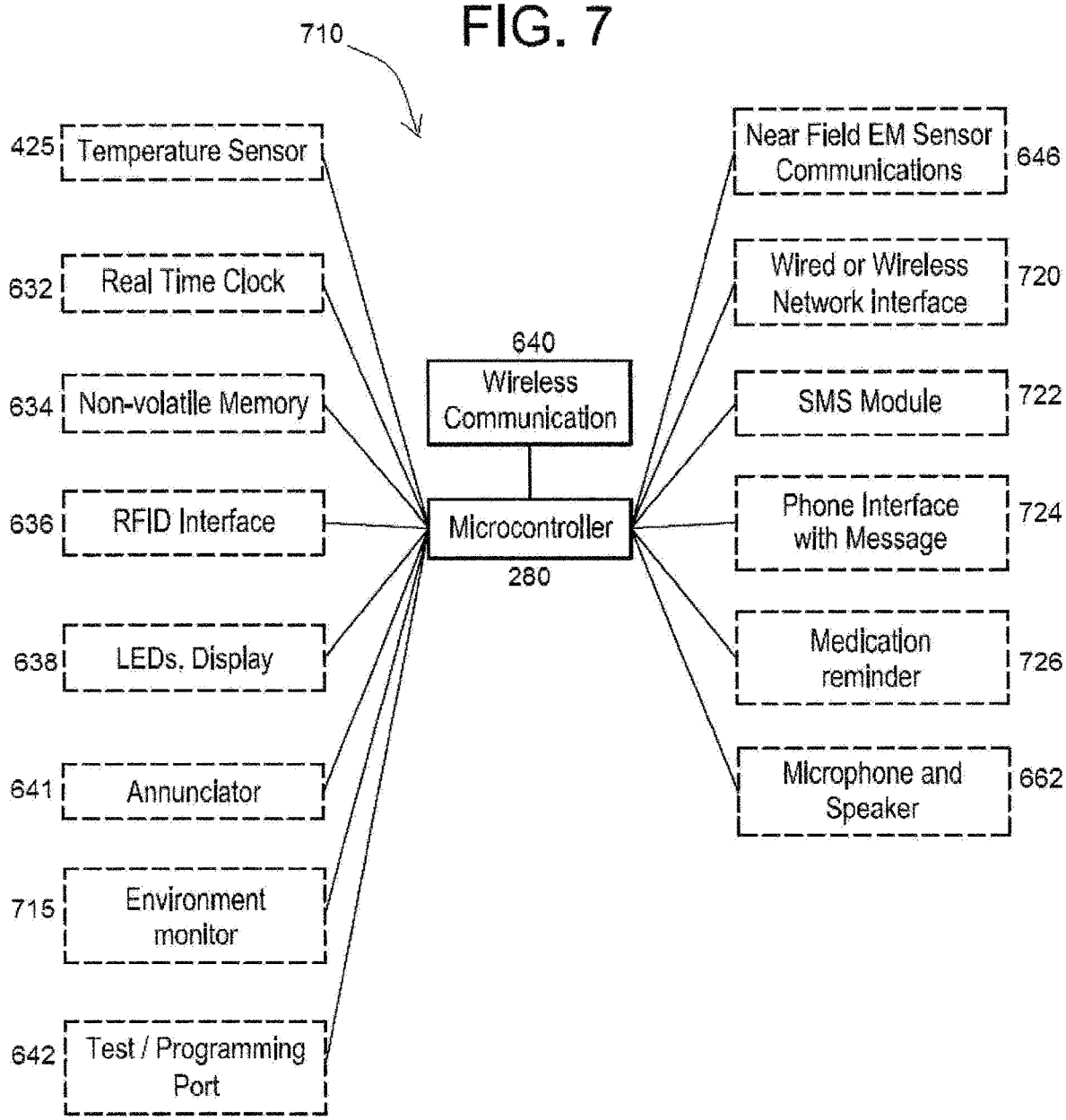
FIG. 7 is a block diagram showing the relationship of certain components of an incontinence monitoring system, according to multiple embodiments and alternatives described herein.

Now turning to FIGS. 6 and 7, further embodiments include a data monitoring, receiving, and tracking sub-system 610, or alternatively 710, which can be configured to monitor and track data specific to an individual patient, a particular tag itself, or the environment around a patient. The data is then transmitted through use of a microcontroller 280 connected to a wireless or other communication module 640 as with previous teachings herein, e.g., Bluetooth connectivity (660) or WiFi. For efficiency, like reference numerals from previous figures are used to identify like components in FIGS. 6 and 7.

In some embodiments, a temperature sensor 425 is placed in tag 200 to sense body temperature which is conducted to the tag along a thermal pathway. Benefits of tracking temperature include having the ability to alert a caregiver of an elevated temperature, which is possibly consistent with an acquired infection. A variety of temperature sensors are known and may be used for obtaining reliable temperature data, including but not limited to a non-contact thermal sensor responsive to infrared heat emanating from the individual.

The temperature sensor 425 can also sense if the tag is attached to the brief. For example, if the tag is removed from the brief for some reason, or not securely fastened and falls off, then it will reflect room temperature which is typically at least 15 to 20 degrees F. below body temperature. This difference in temperature will indicate that attention is needed.

Alternatively, or in conjunction with temperature sensor 425, a motion/position detection sensor 630 is also useful to detect body position relative to a known reference point, such as a bed, and thereby for the discernment of movement or of a possible fall. Such a sensor may include, but is not limited to, gyrometers, tilt sensors, and the like. Other types of biologic sensors can be utilized to sense respiration or seizures, and the data from such sensors can be used to assess medical condition and document care.

In some embodiments, tag 200 may include passive radio frequency identification (RFID) devices for purposes of tracking patients, managing the inventory of tags, or for configuring other systems with unique identifying data from a particular tag. For example an RFID 636 device or barcode on the tag could be used as a tag link 650 to configure a smartphone, tablet, computer to operate with the particular tag. Other near-field electromagnetic sensors 646 can be added to detect tag proximity and allow the main communication system to sense proximity data, including attached sensors 646 to hospital beds, to indicate for example that the bed is in its high position (thus an accident more likely to happen) or its low, dismount position (thus an accident is less likely to happen). In some embodiments according to FIGS. 6, 7, a pulse oximetry sensor 648 is included as part of the tag for measuring oxygen saturation and pulse rate. Likewise, special conductive strips can be embedded with the fabric of brief 10 to sense wetness 25 and perform a chemical analysis of urine 658 such as pH 652, glucose 656, ketones, nitrites, or proteins. Microphones and speakers 662 provide for remote monitoring and conveying of audible messages. Microcontroller 280 can further be configured to communicate with light sensor 644 incorporated with the tag, for determining if a patient is likely awake or likely asleep.

In some embodiments, sub-systems 610, 710 are equipped with memory 634 and real-time clock 632 functions providing a time stamp to show when the most recent void occurred, and when the most recent changing occurred, providing a "brief change" sensing function 654 as indicated based upon when the spring probe 18 of FIG. 1A and FIG. 1B is disconnected from the post extension 38. The occurrence of events such as voiding and changing can further be depicted through use of a light emitting diode (LED), LCD monitor, or like display 638.

Various other features are contemplated according to multiple embodiments and alternatives. For example, medication reminder sensitive to the opening or closing of a pill box can be configured to communicate with sub-system 710, again via short range or local area network interface (720) as with previous teachings. Similarly, data concerning air quality or temperature in the room can be obtained through use of environmental monitor 715 configured to sense conditions and communicate over a network as described herein. Another beneficial feature is the sending of text messages over an SMS module 722 to caregivers or family members regarding the status of the patient, the rooms, or the tag, or optionally the system can be configured to produce a phone call with automated message according to known techniques and methods.

In view of all the above, it will be appreciated that wetness sensor 25 can be placed internally within disposable brief 10. When snap fitted together as described above, the tag, sensor and brief are mechanically and electrically connected, which also provides a thermal path to the inside of the brief for a more accurate body temperature measurement by directly contacting the skin.

A temperature sensor, as well as other types of sensors of biological activity (collectively referred to herein as either 225 or 425), are optionally placed external to the brief either in contact or proximal to the patient's skin. The optional sensors of biological activity can include, but are not necessarily limited to, temperature sensing, pulse oximetry; pal sensing; glucose monitoring urinalysis for proteins, ketones, nitrites, and like indicators; brief/diaper attachment sensing; motion and positioning sensing. Moreover, additional inputs and features can include (again, in on-limiting fashion) a medication reminder, speaker and microphone for verbal communication with the patient in the roost and environmental monitoring for air quality, any of which need not be positioned in contact with the patient. Some embodiments contain a separate switch incorporated with the tag with functions that include nurse call/cancel call, data entry, functional testing and programming 642, and other similar ancillary functions of the tag which are related to patient information and communication.

The tag transmits to any of a number of devices with computing and/or data transfer capability, including but not limited to pager, personal digital assistant (PDA), small phone, tablet, and personal computer. Data transfer is accomplished via the Internet, private network, or cell tower, among other possibilities. In an environment having older and technically challenged people in nursing homes or their own home that don't have a smart phone, tablet or internet, an embodiment exists in which modems that can plug into the wall and communicate directly to the brief 10 with the tag 200 and cell towers.

The tag relies upon a source of power which can be either supplied or renewable. Rechargeable cells or a wireless power circuit connected to an external power circuit can be used to achieve a source of power for extended durations. The system is also capable of determining battery status (e.g., low, spent) and providing audible or visual alerts, the latter kind being capable of receipt via LED, SMS message, or email. In certain embodiments, machine status is provided according to visual or audible signs emanating from a warning panel 641, i.e., annunciator panel providing additional real-time information concerning the status of the tag, its battery, or various other components.

The system is also configurable to provide real-time information of void status, battery status, or biologic activity to caregivers and family members alike, as well as documenting the time when events occur including the changing of a person's brief. Further, there are times when a patient may wander from his or her bed or room, and the system is optionally provided with a motion or positional sensor to indicate such occurrences and notify caregivers or family members with information about a patient's location relative to a reference point such as his or her bed, or the tag on the brief worn by the person has moved out of range of the receiver.

While the embodiments herein are not limited in terms of size and scale, the tag is preferably less than about 1 inch in diameter and less than about 4/10 of an inch in thickness, and it preferably has a range of 100 feet to 300 feet.

FIG. 8 shows a flowchart of how the system could be manufactured.

Figure 9:
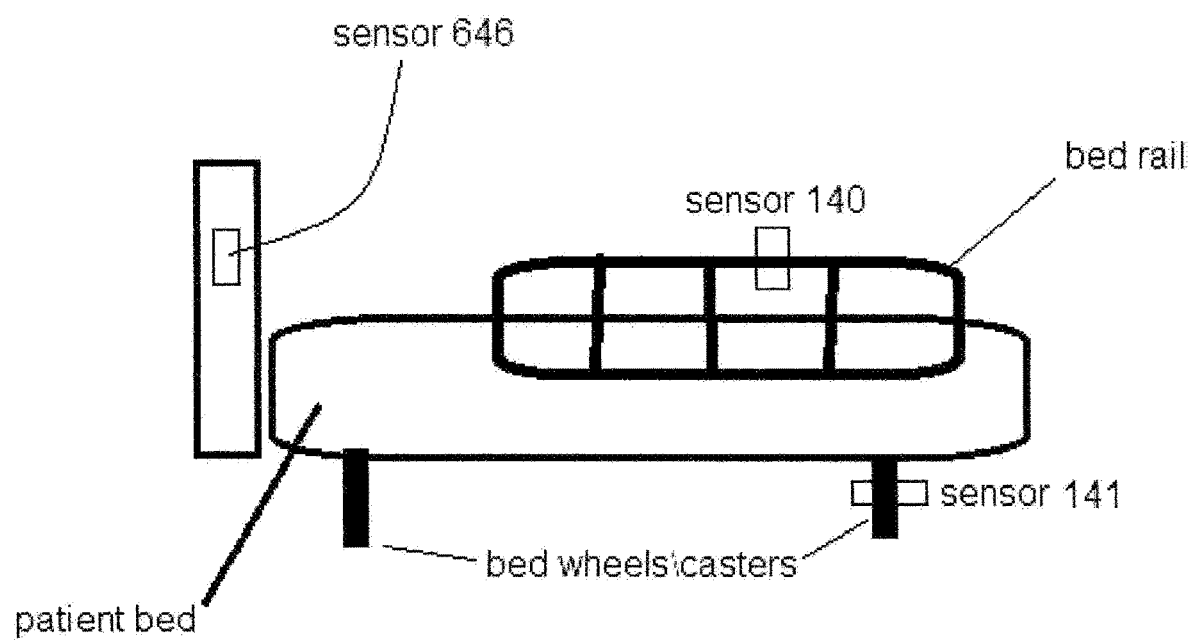
FIG. 9 shows a further embodiment of the system involving additional sensors connected to a patient-bed.

FIG. 9 shows an embodiment in which sensors 140 & 141 can be placed on a patient's bed. These sensors 140 & 141 can be in communication with the tag within the patient's brief 10, but also can independently communicate with the e.g. external computing device 380, Internet cell tower 295 and devices-n (300, 301, 302 . . . ). The sensors 140 & 141 can communicate a variety of information, including but not limited to the bed rail being lowered (140), the wheels/casters being, unlocked, or moved (141) or other errant patient behavior. Further, as discussed earlier, the sensor 140 can be programmed to send an alert to external computing device 380, Internet cell tower 295 and devices1-n (300, 301, 302 . . . ) in the event a pre-determined distance between the tag within the patient's brief 10 and the sensor 140 is exceeded. A type of "invisible fence" for humans.

The distances and warning-intensities can be varied depending on specific environments where the present embodiments are installed. Some environments may prefer no alarm message be sent until the patient is 25-40 feet from their bed, while other environments may prefer a distance of 15 feet. Further, the warning-intensities can also be varied, where a lower-warning can be sent if a patient is moving toward a safe place such as a nurse's station, bathroom, or other permitted resource, while a different warning-intensity can be given if the patient is moving toward e.g. a staircase, or other type of off-limits areas.

Mobile Embodiment(s)

Figure 10:
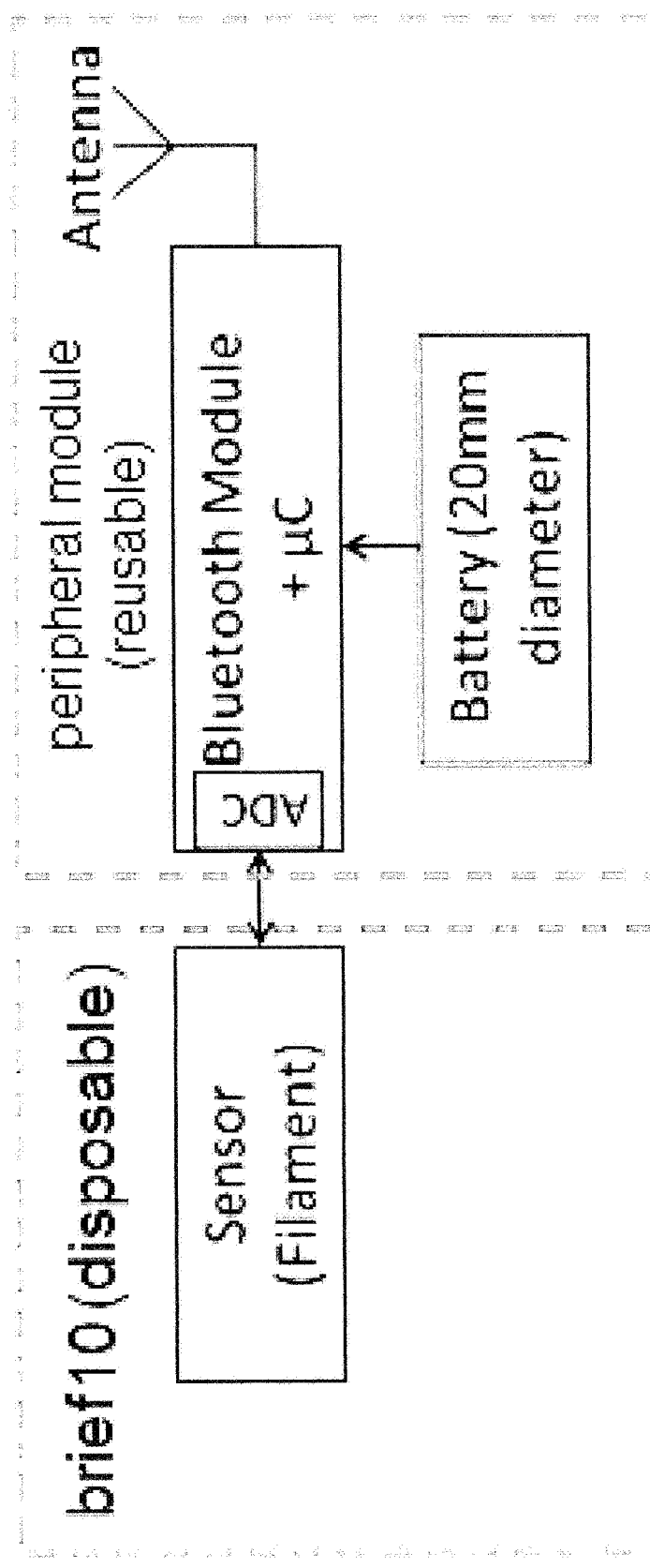
FIG. 10 shows a block diagram including a peripheral module.

A mobile embodiment incorporating the tag 200 and other elements disclosed herein will now be described. This embodiment consists of at least three modules comprising a Peripheral, a Master and a Server. The peripheral module is a microcontroller connected to a moisture\temperature sensor 425 located inside the brief 10, and a Bluetooth Low Energy (BLE) module that communicates with the master module. The peripheral module is also equipped with a coin cell battery. FIG. 10 shows a block diagram including the peripheral module.

The moisture sensor 425 is part of the brief 10 and is therefore disposable. The peripheral module is reusable and con reconnected to the sensor (diaper) using two snaps. These snaps will also provide the electrical connection to the embedded moisture sensor. The sensor is composed of at least two conductive threads 28, 29 sewed within the absorbing material of the brief 10. The two threads 28, 29 are therefore connected to each other through the very high resistivity of the absorbing material. When the brief 10 becomes moist (e.g. when a void occurs), the resistivity of the absorbing material reduces dramatically. When measuring the resistance of the filament/diaper system, the peripheral module can detect as little as 10 mL of water poured into the diaper.

The peripheral module reads the value of the sensor and inserts it into a Bluetooth Low Energy advertisement report. Since there is no connection needed for advertisement, the current drawn by the module is minimized. The microcontroller embedded in the Bluetooth module is programmed with an event driven language which also helps reducing the current consumption: the microcontroller automatically goes to asleep between events. The average current is 7 uA. The energy needed for a whole year is then 60 mAh (7uAh*24 h*365 days). As such, using a CR2032 coin cell battery (with a capacity of about 200 mAh), we obtain a lifetime of 3 years and 4 months.

The master module can be, for example, an iPad or iPhone. The master module receives the information from the peripheral module and shows it into two graphs. These graphs display, for example, the diaper moisture and temperature measurements for the last 24 hours. The master module also makes a TCP connection over a wireless network (e.g. WiFi) with the server and sends the temperature and moisture values stamped with the respective time and date. This connection is only made when these values exceed a predefined threshold or returns back to the normal values. At the same time, the iPad/iPhone alerts the caregiver and/or family member of the event. The developed app for iPhone/iPad also show is the received signal strength from the BLE peripheral and will alert the care giver or family member when out of range of the transmitter. The server module, which can be a PC located in the hospital or a virtual private server on a host such as Amazon, records this information into a database to be used for statistical analysis.

The server module can also generate an automatic email and sends it to the desired email addresses using SMTP (Simple Mail Transfer Protocol) protocol when an important event occurs.

The server configuration can be as follows. When server software (setup.exe) is installed, a user will see console window automatically. The console winds shows the local host IP address, shown in FIG. 11A. For example the IP address of local host m FIG. 11A is 10.200.203.12 After entering the port number (an integer value in the range of [1-1023]), a user will see "Server is Ready for Next TCP Connection" as shown in FIG. 11B. This message means the server program is ready for receiving upcoming TCP connection from iPad/iPhones.

The systems and embodiments disclosed herein further comprise two mobile apps, HHMiPad and HHMiPhone for iPad and iPhone respectively. When a user runs either app, they will see two tabs, Main and Configuration, on the screen. FIGS. 12 and 13 show example Configuration tabs of iPad and iPhone, respectively. The "Peripheral Name" textbox is for a user to specify the peripheral name which will be monitored by the aster module.

The "Threshold" textbox allows a user to adjust a threshold value for moisture sensor. Moisture values higher than the threshold are considered as "wet filament" and values lower than the threshold are considered as "dry filament". When the user adjusts and saves these two items, the HHMiPad or HHMiPhone apps starts monitoring the peripheral.

FIGS. 14 and 15 show in the Main tab that HHMiPad or HHMiPhone apps receive moisture and temperature values every ten seconds and display them on two graphs. As shown in FIGS. 14 and 15, a also see the Bluetooth signal strength in the right if the page. If the iPad/iPhone doesn't receive data from the peripheral module, the user should ensure the iPad/iPhone Bluetooth is set to "on".

The configuration tabs Receiver Email Address, Server IP address and Server Port Number are used for automatic Email transmission. First specify the Server IP address and the Server Port Number. The Server Port Number should be the same as the value inserted as Port Number in server configuration. Meanwhile, within, the Receiver Email Address textbox, a user can specify one or more Email addresses of the persons who are going to receives updated information from the peripheral when an important event occurs.

When a user enters these items, they can turn on the Automatic Email switch so that the HHMiPad or HHMiPhone establishes a TCP connection to the Server to generate and send Entails to the receivers, e.g. when an important event occurs.

Additional features of the invention can include, but are not limited to, using one or more snaps to connect the electronic tag electrically from an outside of the brief to an inside of the brief or pad. Additionally, using one or more snaps to connect the electronic tag electrically from an outside of the brief to an inside of the brief or pad. Additionally, using the temperature sensor located in the electronic tag to measure and monitor a relative temperature that varies with body temperature. Additionally, using the temperature sensor located in the electronic tag to measure and monitor a relative temperature difference between the temperature in claim 6 and room temperature to indicate that the tag has not been replaced on the brief. Additionally, using a motion sensor or accelerometer located within the electronic tag to measure a change in gait pattern to indicate an increased likelihood of a future fall. Additionally, using an accelerometer located within the electronic tag to measure a change in acceleration, indicative that a fall has occurred. Additionally, using an anti-bacterial coating on the electronic tag. Additionally, using an RSSI (Receive Signal Strength Indicator) of the base station that communicate to the wireless transceiver located within the electronic tag to measure communication range and limits within a house or facility. Additionally, using an RSSI (Receive Signal Strength Indicator) of the base station that communicates to the wireless transceiver located within the electronic tag to measure when the user has passed certain boundary conditions, such as exited a house or facility.

Other features of the invention can include diagnosing and treating in-house early stage urinary tract infections and decrease unnecessary hospital admissions and avoidable readmissions of residents due to complications and lower cost for healthcare providers. Another feature is an adjustable wetness sensitivity control which can be manually tailored to a specific individual and tracks when a voiding event occurs plus how long it takes before the brief was changed. This feature also helps establish and track individualized voiding patterns. Further, the custom IPad and IPhone apps can transmit occurrences of voiding, body temperature, location and fall detection to caregivers and help document clinical information. Further, the system electronically develops individualized resident toileting schedules and signals caregivers take residents to be toileted.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways. Also, it is to be u understood that words and phrases used herein are for the purpose of description and should not be regarded as limiting. The use herein of such words and phrases as "such as," "comprising," "e.g.," "containing," or "having" and variations of those words is meant to encompass the items listed thereafter, and equivalents of those, as well as additional items. The use of "including" (or, "include," etc.) should be interpreted as "including but not limited to."

Accordingly, the foregoing descriptions of several embodiments and alternatives are meant to illustrate, rather than to serve as limits on the scope of what has been disclosed herein. The descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. A method of using a system for monitoring persons with incontinence, comprising:
   configuring an electronic tag to have a microcontroller and transmitter;
   locating the electronic tag inside an underwear brief;
   the electronic tag being connected to and aware of status of an electrical connection with a plurality of in-brief sensors located in or near to the underwear brief;
   determining and communicating, through the electronic tag, a status of the electronic tag itself as well as the plurality of in-brief sensors;

monitoring the wetness sensor using a conductor located within the underwear brief worn by a person suffering from incontinence;

locating a first plurality of near-field electromagnetic sensors within the electronic tag, the first plurality of near-field electromagnetic sensors suitable for determining tag proximity; and attaching one or more of a second plurality of near-field electromagnetic sensors to a hospital bed and determining whether the bed is in a high or low position.

2. The method of claim 1, further comprising:

locating a plurality of environment-data sensors near to the hospital bed;

the environment-data comprising at least one of temperature, humidity, and lightness/darkness of the patient room.

3. The method of claim 1, further comprising:

the plurality of in-brief sensors comprising one or more motion detectors, one or more GPS detectors, and one or more temperature sensors, all of which communicate patent-status information to and with a master module;

the in-brief sensors monitoring and transmitting to the master module any potential occurrences of voiding, and body temperature;

the motion detectors and GPS detectors monitoring and transmitting to the master module physical geolocation of a patient, and potential fall detection of a patient;

a customized mobile app located within the master module receiving the transmitted occurrences of voiding, body temperature, physical geolocation, and fall detection.

4. The method of claim 3, further comprising:

a data-storage and processing sub-system managing various communication signals related to an individual patient and working with the master module;

opening or closing of a medication box is configured to communicate with the data-storage and processing sub-system.

5. The method of claim 4, further comprising:

configuring the data-storage and processing sub-system to have a visual warning panel capable of providing visual status of the tag battery; and obtaining warnings regarding a battery status of the tag itself and not limited to status of the wearer, utilizing the warning panel.

6. The method of claim 5, further comprising:

assigning a unique identifier to each particular tag;

determining a life cycle for a particular tag;

calculating and displaying how many days until replacement will be needed for that particular tag; and the tag communicating the life cycle information to the master module using bluetooth.

7. The method of claim 3, further comprising:

providing a thermal path directly to the skin of a wearer\patient thereby yielding a body temperature of that wearer\patient.

8. The method of claim 3, further comprising:

configuring one or more of the in-brief sensors to have an adjustable wetness sensitivity control mechanism; and customizing the adjustable wetness sensitivity control to adapt to the physical conditions of a specific individual.

9. The method of claim 8, further comprising:

configuring the master module to have a self-adjusting algorithm;

the self-adjusting algorithm responsive to a specific person's wetness threshold automatically customizing the adjustable wetness sensitivity control below which no signal is sent;

the master module communicating the customized threshold data to the peripheral module; thereby reducing an incidence of false reports of wetness.

10. The method of claim 1, further comprising:

positioning a peripheral module within a tag;

configuring the peripheral module to have Bluetooth capability;

connecting the peripheral module to be in communication with one or more of the plurality of in-brief sensors;

positioning a master module and a server module to be in communication with the plurality of in-brief sensors, and sensors-in-proximity, through the peripheral module; and the peripheral module reading the various values of the in-brief sensors and inserting these values into a Bluetooth Low Energy (BLE) advertisement report.

11. The method of claim 10, further comprising:

the server module recording information from the tags and various sensors into a database configured to manage statistical and empirical data.

12. The method of claim 10, further comprising:

programming a microcontroller embedded in the peripheral module with an event driven language thereby reducing the current consumption;

the microcontroller automatically going asleep between events.

13. The method of claim 10, further comprising:

locating the master module within a tablet or mobile computing device.

14. The method of claim 10, further comprising:

the server module comprising a PC located in the hospital or a virtual private server;

the server module recording patient information into a database to be used for statistical analysis;

the master module making a TCP connection over a wireless network with the server module and sends the temperature and moisture values stamped with the respective time and date; and the master module only making the TCP connection when these values exceed a predefined threshold or when the values return back to a normal value after a re-set.

15. The method of claim 14, further comprising:

positioning a mobile app within the master module;

locating two or more GUI tabs, comprising Main and Configuration, within the mobile app.

16. The method of claim 15, further comprising:

the Main tab receiving moisture and temperature values every ten seconds and displaying the moisture and temperature information within two GUI graphs.

17. The method of claim 10, further comprising:

the server module generating an automatic email and sending to one or more of a plurality of email addresses using SMTP (Simple Mail Transfer Protocol) protocol when an important event occurs.

18. The method of claim 1, further comprising:

tracking information with a particular tag such as the length of time since the battery was last changed or replaced.

* * * * *